US00PP15841P2

(12) United States Plant Patent
Westhoff

(10) Patent No.: US PP15,841 P2
(45) Date of Patent: Jul. 5, 2005

(54) ***CALIBRACHOA* PLANT NAMED 'WESCAWHITE'**

(50) Latin Name: ***Calibrachoa* sp.**
Varietal Denomination: Wescawhite

(75) Inventor: Heinrich Westhoff, Südlohn (DE)

(73) Assignee: Josef und Heinrich Westhoff Gartenbau-Spezialkulturen, Südlohn (DE)

( * ) Notice: Subject to any disclaimer, the term of this patent is extended or adjusted under 35 U.S.C. 154(b) by 0 days.

(21) Appl. No.: 10/919,007

(22) Filed: Aug. 16, 2004

(51) Int. Cl.[7] ..... A01H 5/00
(52) U.S. Cl. ..... Plt./263
(58) Field of Search ..... Plt./263

(56) References Cited

U.S. PATENT DOCUMENTS

PP13,243 P2 * 11/2002 Klemm ..... Plt./263
PP14,070 P2 * 8/2003 Klemm ..... Plt./263
PP14,464 P2 * 1/2004 Pierce ..... Plt./263
PP14,955 P2 * 6/2004 Sakazaki ..... Plt./263

OTHER PUBLICATIONS

UPOV ROM GTITM Computer Database, GTI Jouve Retrieval Software 2004/04 Citation for 'Wescawhite'.* http://www.pac–elsner.com/uk/produkte/produkte–weitere–petunien.html.*

* cited by examiner

*Primary Examiner*—Kent Bell
*Assistant Examiner*—W. C. Haas
(74) *Attorney, Agent, or Firm*—C. A. Whealy

(57) ABSTRACT

A new and distinct cultivar of *Calibrachoa* plant named 'Wescawhite', characterized by its cascading and uniform growth habit; freely branching habit and short internodes; dense and bushy plant form; relatively small leaves; medium-sized flowers; and numerous white-colored flowers with violet-colored venation and circumorbital ring.

1 Drawing Sheet

Botanical designation: *Calibrachoa* sp.
Variety denomination: 'Wescawhite'.

BACKGROUND OF THE INVENTION

The present Invention relates to a new and distinct cultivar of *Calibrachoa* plant, botanically known as *Calibrachoa* sp., and hereinafter referred to by the cultivar name 'Wescawhite'.

The new *Calibrachoa* is a product of a planned breeding program conducted by the Inventor in Südlohn, Germany. The new *Calibrachoa* originated from a cross-pollination made by the Inventor of a proprietary selection of *Calibrachoa* identified as code number 01P442, not patented, as the female, or seed, parent with a proprietary selection of *Calibrachoa* identified as code number 01P432, not patented, as the male, or pollen, parent. The new *Calibrachoa* was discovered and selected by the Inventor in 2002 in a controlled environment in Südlohn, Germany as a single plant within the resulting progeny from the cross-pollination.

Asexual reproduction of the new cultivar by terminal cuttings at Südlohn, Germany since 2002, has shown that the unique features of this new *Calibrachoa* are stable and reproduced true to type in successive generations.

SUMMARY OF THE INVENTION

Plants of the cultivar Wescawhite have not been observed under all possible environmental conditions. The phenotype may vary with variations in environment such as temperature, light intensity and daylength without, however, any variance in genotype.

The following traits have been repeatedly observed and are determined to be the unique characteristics of 'Wescawhite'. These characteristics in combination distinguish 'Wescawhite' as a new and distinct cultivar:

1. Cascading and uniform growth habit.
2. Freely branching habit and short internodes, dense and bushy appearance.
3. Relatively small leaves.
4. Medium-sized flowers.
5. Numerous white-colored flowers with violet-colored venation and circumorbital ring.

Plants of the cultivar Wescawhite can be compared to plants of the female parent selection. In side-by-side comparisons conducted in Südlohn, Germany, plants of the new *Calibrachoa* differed from plants of the female parent selection in the following characteristics:

1. Plants of the new *Calibrachoa* had larger flowers than plants of the female parent selection.
2. Plants of the new *Calibrachoa* and the female parent selection differed in flower color as plants of the female parent selection had light blue-colored flowers.

Plants of the cultivar Wescawhite can be compared to plants of the male parent selection. In side-by-side comparisons conducted in Südlohn, Germany, plants of the new *Calibrachoa* differed from plants of the male parent selection in the following characteristics:

1. Plants of the new *Calibrachoa* had narrower stems than plants of the male parent selection.
2. Plants of the new *Calibrachoa* had smaller leaves than plants of the male parent selection.

3. Plants of the new *Calibrachoa* and the male parent selection differed in flower color as plants of the female parent selection had light blue-colored flowers.

Plants of the new *Calibrachoa* can also be compared to plants of the *Calibrachoa* cultivar Carillon White, not patented. In side-by-side comparisons conducted in Südlohn, Germany, plants of the new *Calibrachoa* differed from plants of the cultivar Carillon White in the following characteristics:

1. Plants of the new *Calibrachoa* had lighter green-colored stems than plants of the cultivar Carillon White.
2. Plants of the new *Calibrachoa* had sessile leaves whereas plants of the cultivar Carillon White had leaves with petioles.
3. Plants of the new *Calibrachoa* and the cultivar Carillon White differed in flower color.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Calibrachoa.*

The photograph at the top of the sheet comprises a side perspective view of typical flowering plants of 'Wescawhite' grown in a container.

The photograph at the bottom of the sheet is a close-up view of typical flowers of 'Wescawhite'.

DETAILED BOTANICAL DESCRIPTION

Plants used in the aforementioned photographs and for the following description were grown under conditions which closely approximate commercial production conditions during the spring and summer in a glass-covered greenhouse in Südlohn, Germany. Plants were about 20 weeks from planting rooted cuttings and grown in containers. During the production of the plants, the day temperatures ranged from 20 to 25° C., night temperatures ranged from 16 to 18° C. and light levels ranged from 3,000 to 50,000 lux.

In the following description, color references are made to The Royal Horticultural Society Colour Chart, 2001 Edition, except where general terms of ordinary dictionary significance are used.

Botanical classification: *Calibrachoa* sp. cultivar Wescawhite.

Parentage:

*Female parent.*—Proprietary selection of *Calibrachoa* sp. identified as 01P442, not patented.

*Male parent.*—Proprietary selection of *Calibrachoa* sp. identified as 01P432, not patented.

Propagation:

*Type cutting.*—Terminal vegetative cuttings.

*Time to initiate roots.*—About 18 to 20 days at 20° C.

*Time to develop roots.*—About 20 to 28 days at 20° C.

*Root description.*—Numerous, fine, fibrous, and well-branched.

Plant description:

*Form.*—Annual flowering plant; cascading; uniform, rounded appearance, plants eventually become spherical in overall shape. Freely branching with lateral branches forming at every node. Vigorous growth habit.

*Usage.*—Appropriate for hanging baskets, window boxes and patio containers.

*Plant height* (*from soil level to top of plant plane*).—About 12 cm.

*Plant length* (*from soil level to lateral branches apices*).—About 60 cm.

*Plant diameter* (*area of spread*).—About 75 cm.

*Stem description.*—Main branches, length: About to 55 to 60 cm. Main branches, diameter: About 2.2 mm. Lateral branches, length: About 16.5 cm. Lateral branches, diameter: About 1 mm. Internode length: About 1.4 cm. Texture: Densely pubescent. Strength: Strong, wiry. Color: 144A.

*Foliage description.*—Arrangement: Before flowering, alternate; after flowering, opposite; simple; sessile. Length: About 2.6 cm. Width: About 8.5 mm. Shape: Elliptic. Apex: Acute. Base: Attenuate. Margin: Entire. Aspect: Mostly flat. Texture, upper and lower surfaces: Densely pubescent. Venation: Pinnate. Color: Developing foliage, upper surface: 146A. Developing foliage, lower surface: 146B. Fully expanded foliage, upper surface: 147A; midvein, 147B. Fully expanded foliage, lower surface: 147B; midvein, 147C.

Flower description:

*Flower type and habit.*—Medium-sized flowers; flowers face upright or outward; single, axillary. Flowers not persistent. Freely flowering with flowers forming at every axil.

*Natural flowering season.*—Spring until frost in the autumn; flowering continuous.

*Flower longevity on the plant.*—About one week.

*Flower size.*—Diameter: About 3.2 cm. Depth (height): About 1.9 cm. Tube length: About 1.4 cm. Throat diameter, distal end: About 9 mm. Tube diameter, proximal end: About 3.4 mm.

*Flower buds.*—Length: About 1.8 cm. Diameter: About 6 mm. Shape: Oblong. Color: Towards the base, 1C, venation, 166A; mid-section, 82C, venation, 166A; towards the apex, 155B, venation, 166A.

*Corolla.*—Arrangement/appearance: Single whorl of five petals, fused into flared trumpet. Petal length from throat: About 1.4 cm. Petal width: About 1.5 cm. Petal shape: Roughly spatulate with rounded to slightly acute apex. Petal margin: Entire. Petal texture, upper and lower surfaces: Smooth, satiny. Color: Petal, when opening and fully opened, upper surface: Lighter than N155D; circumorbital ring, 86B; venation, 86A. Color becoming closer to 158D with development. Petal, when opening and fully opened, lower surface: N155D; venation, N77A. Flower throat (inside): 12B; venation, N77A. Flower tube (outside): 11C to 11D; venation, N77A.

*Sepals.*—Arrangement/appearance: Single whorl of five sepals, star-shaped. Length: About 1.45 cm. Width: About 3.2 mm. Shape: Lanceolate. Apex: Acute. Margin: Entire. Texture, upper and lower surfaces: Pubescent. Color, upper and lower surfaces: 146A.

*Peduncles.*—Length: About 2 cm. Width: About 0.9 mm. Strength: Flexible, wiry. Texture: Pubescent. Color: 144A.

*Reproductive organs.*—Stamens: Quantity per flower: Five. Anther shape: Four-parted, ovate. Anther length: About 2 mm. Anther diameter: About 1.5 mm. Filament length: About 5 mm. Filament color: 145C. Anther color: 8B. Pollen amount: Moderate. Pollen color: 8B. Pistils: Quantity per flower: One. Pistil length: About 7 mm. Stigma shape: Ovate. Stigma color: 144A. Style length: About 5 mm. Style color: 144C. Ovary color: 144C.

*Seed/fruit.*—Seed and fruit production has not been observed.

Disease/pest resistance: Plants of the new *Calibrachoa* have not been noted to be resistant to pathogens and pests common to *Calibrachoa*.

Temperature tolerance: Plants of the new *Calibrachoa* have been observed to be tolerant to temperatures ranging from 2 to 30° C.

It is claimed:

1. A new and distinct cultivar of *Calibrachoa* plant named 'Wescawhite', as illustrated and described.

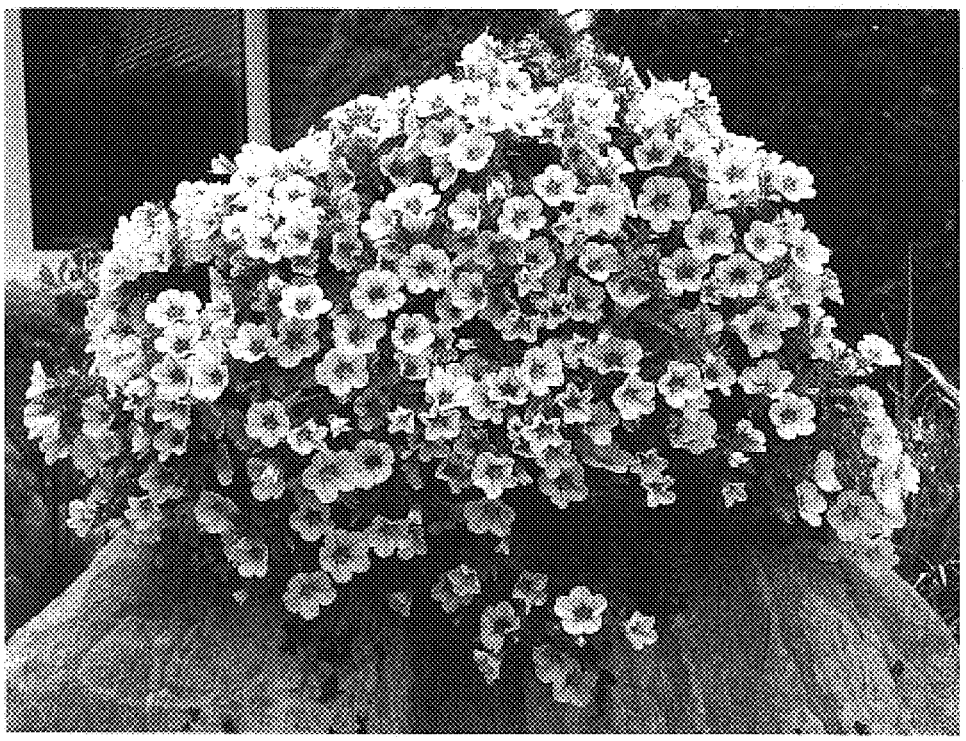
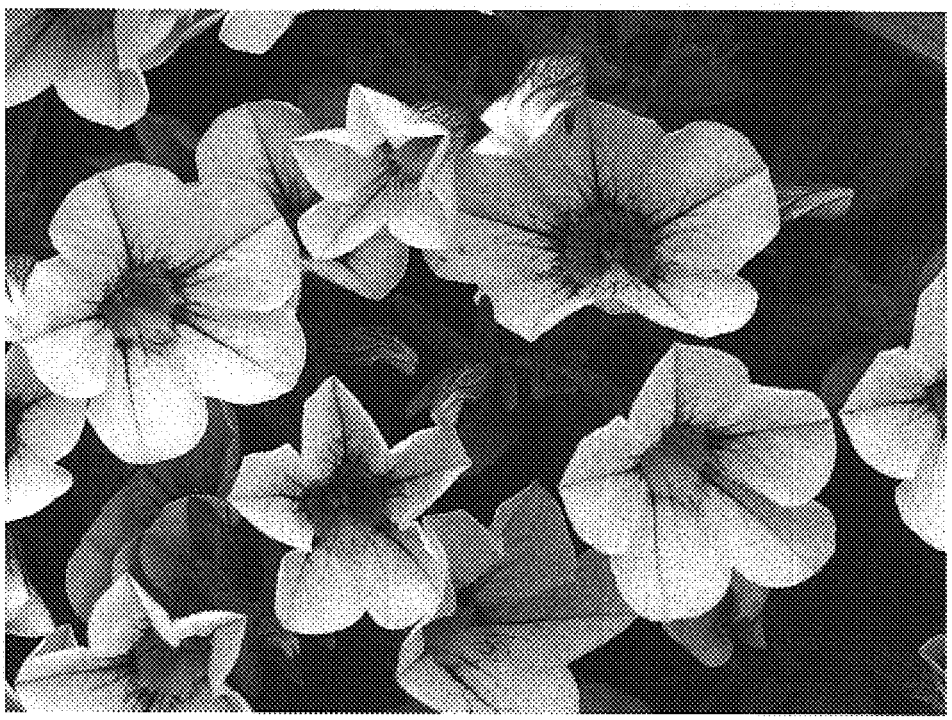

* * * * *